(12) United States Patent
Firmbach et al.

(10) Patent No.: US 12,408,930 B2
(45) Date of Patent: Sep. 9, 2025

(54) SURGICAL INSTRUMENT AND SURGICAL INSTRUMENT SYSTEM

(71) Applicant: Aesculap AG, Tuttlingen (DE)

(72) Inventors: Franz-Peter Firmbach, Emmingen-Liptingen (DE); Lilli Stoffels, Calw (DE)

(73) Assignee: Aesculap AG, Tuttlingen (DE)

( * ) Notice: Subject to any disclaimer, the term of this patent is extended or adjusted under 35 U.S.C. 154(b) by 253 days.

(21) Appl. No.: 18/347,974

(22) Filed: Jul. 6, 2023

(65) Prior Publication Data

US 2024/0023971 A1 Jan. 25, 2024

(30) Foreign Application Priority Data

Jul. 25, 2022 (DE) ...................... 10 2022 207 576.5

(51) Int. Cl.
*A61B 17/15* (2006.01)
*A61B 17/00* (2006.01)
*A61B 90/00* (2016.01)

(52) U.S. Cl.
CPC .. *A61B 17/157* (2013.01); *A61B 2017/00128* (2013.01); *A61B 2090/067* (2016.02)

(58) Field of Classification Search
CPC .. A61B 17/157; A61B 17/155; A61B 17/1764
See application file for complete search history.

(56) References Cited

U.S. PATENT DOCUMENTS

| | | | |
|---|---|---|---|
| 2010/0305711 A1* | 12/2010 | McKinnon | A61B 17/157 606/82 |
| 2015/0045801 A1 | 2/2015 | Axelson, Jr. et al. | |
| 2021/0000484 A1 | 1/2021 | Goble et al. | |

FOREIGN PATENT DOCUMENTS

| | | |
|---|---|---|
| AU | 2010283577 A1 | 2/2012 |
| WO | 0000093 A1 | 1/2000 |
| WO | 2011018647 A1 | 2/2011 |

* cited by examiner

*Primary Examiner* — Samuel S Hanna
(74) *Attorney, Agent, or Firm* — Christopher A. Rothe; CM Law (57) ABSTRACT

A surgical instrument for use in a knee joint replacement operation having a first fastening device, a second fastening device, a guiding device connected at one end to the first fastening device and at the other end to the second fastening device and by which the second fastening device is pivotably movable in a manner guided relative to the first fastening device in a sagittal guiding plane, and an alignment rod configured for alignment with respect to an anterior edge of a tibia. The alignment rod is releasably connected to the second fastening device in a rigid manner.

12 Claims, 4 Drawing Sheets

SURGICAL INSTRUMENT AND SURGICAL INSTRUMENT SYSTEM

CROSS-REFERENCE TO RELATED APPLICATION(S)

This application claims priority under 35 U.S.C. § 119 to German Application No. 10 2022 207 576.5, filed on Jul. 25, 2022, the content of which is incorporated by reference herein in its entirety.

FIELD

The present disclosure relates to a surgical instrument for use in a knee joint replacement operation. The present disclosure further relates to a surgical instrument system having such a surgical instrument.

BACKGROUND

In a knee joint replacement operation (total knee arthroplasty (TKA)), joint surfaces of the femur and/or tibia which have become worn or otherwise damaged by disease or an accident are replaced by means of artificial joint surfaces of a knee joint prosthesis. Such knee joint prostheses generally comprise a femoral component and a tibial component. The femoral component is implanted at the distal end of the femur. The tibial component is implanted at the proximal end of the tibia.

Prior to the implantation of the prosthetic components, the distal femur and the proximal tibia are resected. To this end, the surgeon makes various resection cuts and separates bone and/or cartilage material from the respective bone. As a result of the resection, the respective bone is adapted in terms of its shape to the prosthetic component which is intended to be received.

The resection can be carried out on the basis of various concepts. One concept is intended to keep the tensions of the ligaments of the knee balanced during the joint movement. A better function of the knee joint prosthesis is thereby intended to be ensured. This concept is generally referred to as "gap balancing". In other concepts, the surgeon removes by means of resection a specific quantity of bone and/or cartilage material. Such concepts are generally referred to as "measured resection". The orientation of the resection cuts with respect to the anatomy of the patient determines the subsequent orientation of the implanted components and consequently also the orientation of the prosthetic joint axes. The alignment of the resection cuts is therefore particularly significant.

In the alignment of the resection cuts, there are mainly three approaches: mechanical, anatomical and kinematic. In the mechanical alignment, the proximal tibia is resected perpendicularly to the longitudinal axis of the tibia shaft. The resection of the distal femur is accordingly carried out in a manner adapted thereto. If necessary, ligament releases are carried out. In the anatomical alignment, an attempt is made to resect the tibia at a varus angle of 3°. The femur resection and ligament releases are carried out with the objective of a straight hip/knee/ankle axis of the leg. The objective of the kinematic alignment (abbreviated below to KA) is to implant the synthetic joint surfaces of the prosthetic components at the level of the pre-arthritic defect-free natural joint surfaces.

In KA, the alignment of the resection cuts is often carried out from the distal femur. The resection of the proximal tibia is carried out in a manner adapted thereto. In this context, a transfer of the alignment and/or cuts is also referred to. To this end, specific surgical instruments which are also referred to as tibial cut alignment guides are known. Such instruments enable a transfer of the alignment of the femoral resection cuts to the tibia. The transfer is generally carried out after an at least distal resection of the femur, in which the distal condyles are separated. The transfer can be carried out in extension or flexion. In a variant of the KA, the distal femur is initially completely prepared (all femur first). In this instance, the resection cuts which are intended to be carried out on the distal femur are aligned with respect to the anatomy of the patient and applied to the distal femur. Subsequently, a femoral trial condyle implant is applied to the distal femur. The femoral trial condyle implant which is already orientated in accordance with the anatomy of the patient is then used as a reference component, the alignment of which is transferred by means of the surgical instrument or transfer tool to the proximal tibia in order to align and apply the resection cuts which are intended to be carried out thereon.

Such surgical instruments generally have a plurality of guides and/or bearings which connect various components of the respective surgical instrument to each other so as to be able to be movable in terms of adjustment in order to enable an adaptation to given anatomical specific features of the patient. Such guides or bearings are complex to adjust when the surgical instrument is used during the knee joint replacement operation. Furthermore, the guiding or bearing tolerances present add up in the manner of a tolerance chain, which is detrimental to a precise alignment transfer to the proximal tibia.

SUMMARY

An object of the present disclosure is to provide a surgical instrument and a surgical instrument system which afford advantages with respect to conventional surgical instruments and surgical instrument systems and which in particular enable a particularly precise alignment of the resection cuts which are intended to be carried out at the tibial side starting from a reference component which is fixed at the femoral side.

The surgical instrument according to the present disclosure is intended for use in a knee joint replacement operation and has: a first fastening device which is configured for releasable fastening to a reference component which is fitted to a distal femur, a second fastening device which is distally spaced apart from the first fastening device and which is configured for releasable fastening to a tibia cutting block for guiding cutting on a proximal tibia, a guiding device which is connected at one end to the first fastening device and at the other end to the second fastening device and by means of which the second fastening device is pivotably movable in a manner guided relative to the first fastening device in a sagittal guiding plane, and an alignment rod which is configured for alignment with respect to an anterior edge of the tibia, wherein the alignment rod is releasably connected to the second fastening device in a rigid manner, in particular in a rotationally and/or pivotably rigid manner. The surgical instrument according to the present disclosure has a particularly low number of guides or bearings which connect the components of the surgical instrument to each other in an adjustably movable manner. With the surgical instrument according to the present disclosure, a pivotably movable support of the alignment rod on the second fastening device is dispensed with. The surgical instrument is consequently particularly robust and torsion-resistant. This enables a particularly precise transfer of the orientation or alignment of the reference component to the tibia cutting block. During the use of the surgical instrument, the first fastening device is releasably fastened to the reference component which is fitted at the femur side and the tibia cutting block is releasably fastened to the second fastening device. The reference component is preferably a femoral trial condyle implant. In this instance, the surgical instrument is particularly suitable for use in the "all femur first" variant of the KA. Alternatively, the reference component may be a distal femoral cutting block for distal cut guiding on the femur or the like. Neither the reference component nor the tibia cutting block are a component of the surgical instrument according to the present disclosure. The guiding device enables a guided pivot movement of the second fastening device relative to the first fastening device. In the use of the surgical instrument, the guiding device consequently enables an accordingly guided relative movement of the tibia cutting block with respect to the femur-side reference component. The inclination of the tibia cutting block in the guiding plane can thereby be adjusted. The guiding plane is orientated in a sagittal manner and consequently extends in an anteroposterior and proximodistal manner. Preferably, a pivot axis about which the two fastening devices are guided relative to each other in a pivotably movable manner by means of the guiding device intersects with a mechanical tibia axis in the sagittal guiding plane. The inclination mentioned is also referred to as a posterior or anterior slope. The adjustability of the inclination of the tibia cutting block—referred to below as slope for short—enables, on the one hand, an adaptation to preoperatively determined parameters. On the other hand, an actually prevalent flexion or extension position of the leg as a result of the movability of the guiding device can be taken into account and compensated for. It can thereby be ensured that an adjustment of the slope does not at the same time lead to an undesirable change of a proximodistal position of the tibia cutting block and consequently a so-called tibia cutting height.

The position and direction designations used in this description refer to the body of a patient, in particular the patient's femur, and are thus intended to be understood in accordance with their conventional anatomical meaning. Consequently, "anterior" means front or located at the front, "posterior" means rear or located at the rear, "medial" means inner or located at the inner side, "lateral" means outer or located at the outer side, "proximal" means in the direction towards the centre of the body and "distal" means remote from the body centre. Furthermore, "proximodistal" means along, preferably parallel with, a proximal/distal axis, "anteroposterior" means along, preferably parallel with, an anterior/posterior axis and "mediolateral" means along, preferably parallel with, a medial/lateral axis. Said axes are orientated orthogonally with respect to each other and can of course be placed with reference to X, Y and Z axes which are not connected with the anatomy of the patient. For example, the proximal/distal axis may alternatively be referred to as the X axis. The medial/lateral axis may be referred to as a Y axis. The anterior/posterior axis can be referred to as a Z axis. For improved illustration and for the sake of simplicity, the mentioned anatomical position and direction designations are used primarily below.

In one embodiment of the present disclosure, the second fastening device has a receiving portion in which a fastening portion of the alignment rod is received in a receiving direction. This enables, in a manner which is particularly simple to implement, the rigid releasable connection of the alignment rod to the second fastening device. The receiving portion and the fastening portion can be adapted to each other in terms of dimensions in the manner of a narrow clearance fit or a transition fit in order to ensure easy assembly and disassembly of the alignment rod.

In another embodiment of the present disclosure, the fastening portion of the alignment rod has at least in a part-portion a non-round, preferably angular, in a particularly preferred manner rectangular, cross section, wherein the receiving portion of the second fastening device has a shape which is constructed for releasable rigid connection of the alignment rod and the second fastening device so as to complement the fastening portion, in particular at least the part-portion of the alignment rod. Between the receiving portion and fastening portion there is consequently a positive-locking connection (form-fit) which prevents a rotation of the mounted alignment rod about a longitudinal axis of the fastening portion relative to the second fastening device In another embodiment of the present disclosure, the non-round cross section is constructed in a rotationally symmetrical, in particular point-symmetrical manner so that the alignment rod can be received for releasable rigid connection to the second fastening device in at least two angular positions relative to the second fastening device in the receiving portion thereof. The alignment rod can thus be mounted in a plurality of different angular positions relative to the second fastening device. Preferably, the alignment rod can be mounted relative to the second fastening device in two angular positions which are rotated through 180° with respect to each other. Consequently, one and the same alignment rod, particularly when having a rotationally non-symmetrical shape, can be used for a knee joint replacement operation both on the right leg and on the left leg.

In another embodiment of the present disclosure, the alignment rod is curved in an S-shaped manner. Such an alignment rod advantageously follows the anatomy of the anterior edge of the tibia so that it can be aligned in a particularly precise manner on the anterior edge of the tibia.

In another embodiment of the present disclosure, the second fastening device has a handling portion, the shape of which is adapted to an anatomy of a human hand. This improves the handling of the surgical instrument. In particular, the handling portion enables a particularly secure grip, which is fatigue-free for the surgeon, of the surgical instrument.

In another embodiment of the present disclosure, the second fastening device comprises a, in particular plate-like, base member, on which in order to form the handling portion there is provided a recess which is constructed to receive at least one finger. Such a handling portion which is formed by the recess can be produced in a particularly simple manner. In addition, ergonomic advantages are afforded.

In another embodiment of the present disclosure, there is provided a display device which is configured to display an angular position of the second fastening device in the guiding plane relative to the first fastening device. This angular position corresponds in the assembled state of the alignment rod to the angular position thereof relative to the first fastening device. The display device consequently enables a reading of a current flexion angle of the femur relative to the tibia. Based on this flexion angle, the slope can further be adjusted in a particularly intuitive manner before the proximal tibia is resected. Before the resection of the tibia, the alignment rod can preferably be disassembled for better accessibility.

In another embodiment of the present disclosure, the display device comprises at least one scale and at least one reading mark, wherein the scale is connected to the first fastening device and the reading mark is connected to the guiding device, or vice versa, and wherein a position of the reading mark relative to the scale represents the current angular position of the second fastening device in the guiding plane relative to the first fastening device. This embodiment is structurally simple and additionally enables a simple and rapid visual detection of the angular position.

In another embodiment of the present disclosure, the guiding device has at least one curved guiding rod and a guide receiving member in which the guiding rod is received in a state guided in a slidingly movable manner, wherein the guide receiving member is connected to the first fastening device and the guiding rod is connected to the second fastening device, or vice versa, and wherein the second fastening device is guided in a linearly movable manner by means of the guiding device along a guiding path which is elongate in a circular-arc-like manner relative to the first fastening device. Such a guiding device can also be described as a circular guide. It enables the pivotably movable connection of the two fastening devices about a notional (virtual) pivot axis which is arranged with spacing from the guiding device.

In another embodiment of the present disclosure, there is provided a first linear guide by means of which the guiding device is connected to the first fastening device and is linearly movable in a manner guided relative thereto in the guiding plane along a first guiding path which is elongate in an anteroposterior manner. The first linear guide advantageously enables the pivot axis of the two fastening devices to be adjusted. Consequently, in particular the position of the pivot axis can be adapted to the anatomy of the patient.

In another embodiment of the present disclosure, there is provided a second linear guide, by means of which the second fastening device is connected to the guiding device and is linearly movable in a manner guided relative thereto in the guiding plane along a second guiding path which is elongate in an anteroposterior manner. Consequently, an anteroposterior position of the second fastening device can be adapted to the anatomy of the patient, in particular to the size of the tibia. An undesirable change of the anteroposterior position of the guiding device is avoided in this instance. The same applies accordingly to the positioning of the tibia cutting block when it is secured to the second fastening device.

In another embodiment of the present disclosure, a fixing device is provided and is configured to fix the movability of the guiding device. Consequently, the tibia cutting block after completed alignment with respect to the reference component can be fixed in the position thereof. This enables a particularly secure guiding of a surgical cutting tool when a resection cut is made to the tibia.

The present disclosure further relates to a surgical instrument system having a surgical instrument according to the present disclosure. The surgical instrument system further comprises a reference component which is releasably fastened to the first fastening device of the surgical instrument and a tibia cutting block which is releasably fastened to the second fastening device of the surgical instrument. The advantages explained above of the surgical instrument according to the present disclosure can also be transferred mutatis mutandis to the surgical instrument system according to the present disclosure.

Of course, the features which have been mentioned above and those which will be explained below can be used not only in the combination set out, but also in other combinations or alone without departing from the scope of the present disclosure.

BRIEF DESCRIPTION OF THE DRAWINGS

Other advantages and features of the present disclosure will be appreciated from the following description of a preferred embodiment of the present disclosure which is illustrated with reference to the drawings.

DETAILED DESCRIPTION

Figure 1:
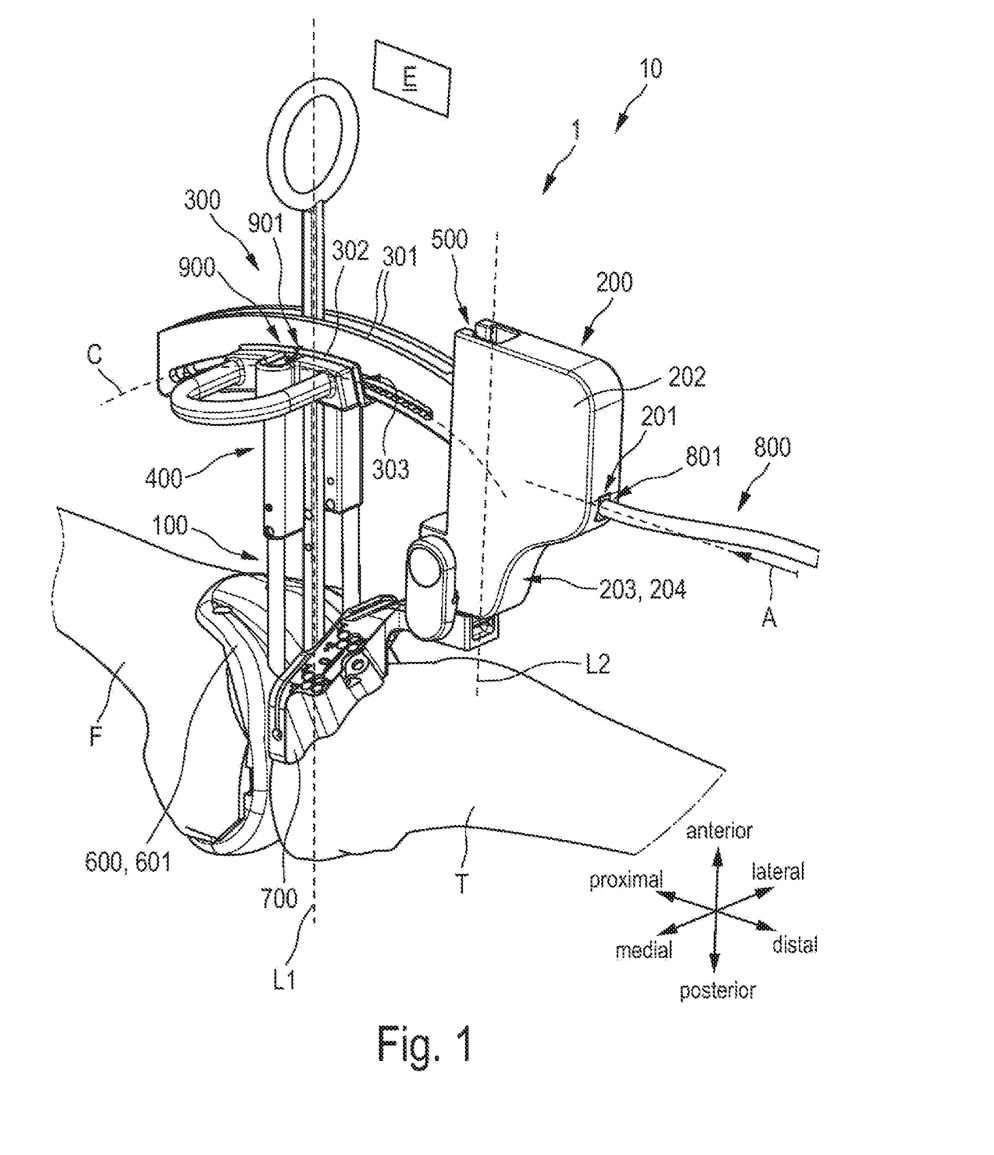
FIG. 1 shows a schematic, perspective view of an embodiment of a surgical instrument according to the present disclosure in an intraoperative situation, in which the surgical instrument is fastened at one end to a femoral trial condyle implant which acts as a reference component and at the other end to a proximal tibia cutting block.
Figure 2:
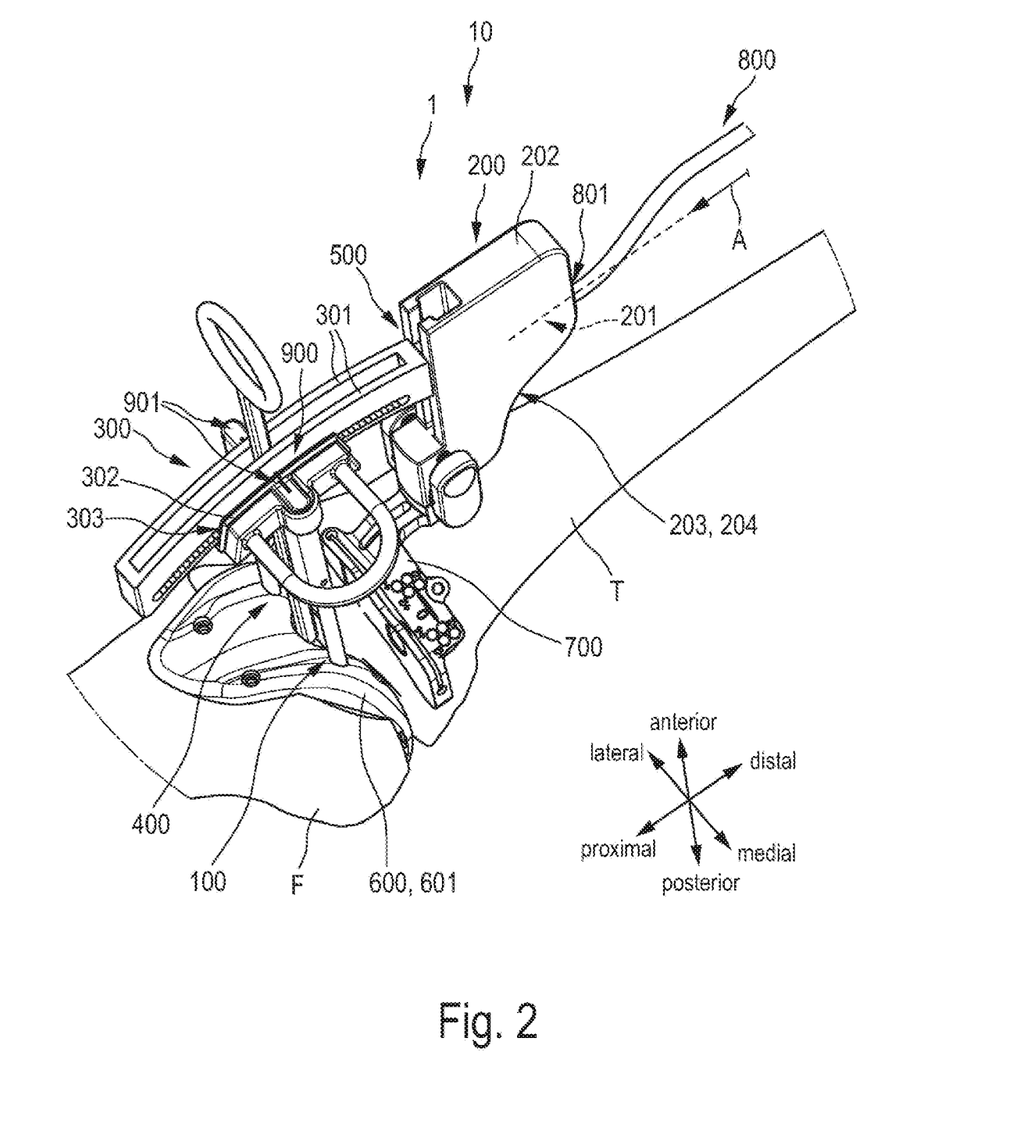
FIG. 2 shows a schematic, perspective view of the intraoperative situation shown in FIG. 1 from another viewing angle.

According to FIGS. 1 and 2, a surgical instrument 1 for use in a knee joint replacement operation is provided. The surgical instrument 1 can also be referred to as a transfer tool or tibia transfer tool. It is used for referenced positioning of a tibia cutting block 700 on a proximal tibia T. A reference component 600 which has already been positioned on a distal femur F is used as a reference for the position of the tibia cutting block 700. In the intraoperative situation shown in FIGS. 1 and 2, the distal femur F is already completely prepared and provided with a trial condyle implant 601 which acts as a reference component 600. Before the femoral trial condyle implant 601 was arranged on the distal femur F, all the necessary resection cuts were applied to the femur F. The intraoperative situation shown therefore relates to a so-called all femur first operation method, which is characterised in that the distal femur F is completely prepared before any measures are carried out on a proximal tibia T. Alternatively to the femoral trial condyle implant 601, a femur cutting block can also be used as a reference component 600 if the surgeon takes an approach other than the all femur first approach.

The reference component 600 and the femoral trial condyle implant 601 are not a component of the surgical instrument 1. The tibia cutting block 700 which is configured for guiding cutting at the proximal tibia T is not a component of the surgical instrument 1.

The surgical instrument 1 forms together with the reference component 600 and with the tibia cutting block 700 a surgical instrument system 10.

The surgical instrument 1 comprises a first fastening device 100, a second fastening device 200, a guiding device 300 and an alignment rod 800.

The first fastening device 100 is configured for releasable fastening to the reference component 600. The second fastening device 200 is distally spaced apart from the first fastening device 100. The second fastening device 200 is configured for releasable fastening to the tibia cutting block 700. In the intraoperative situation shown in FIGS. 1 and 2, the first fastening device 100 is releasably fastened to the reference component 600 and the second fastening device 200 is releasably fastened to the tibia cutting block 700.

The guiding device 300 is connected at one end to the first fastening device 100 and at the other end to the second fastening device 200. The connection of the guiding device 300 to the first fastening device 100 and—alternatively or additionally—to the second fastening device 200 can be constructed in a releasable manner. In this instance, the second fastening device 200 is guided by means of the guiding device 300 relative to the first fastening device 100 in a sagittal guiding plane E in a pivotably movable manner. Consequently, the guiding device 300 enables the second fastening device 200 to be able to be positioned in a manner guided within the sagittal guiding plane E at an angle relative to the first fastening device 100.

Figures 3, 4:
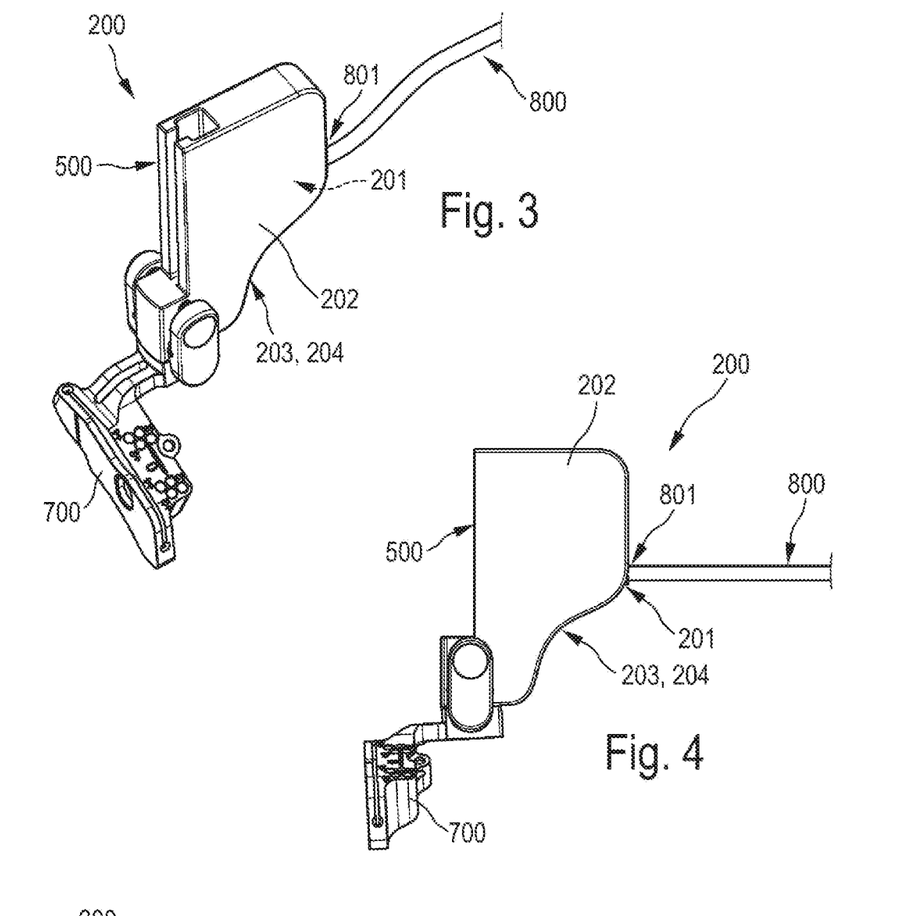
FIG. 3 shows a schematic, perspective view of a disassembled second fastening device of the surgical instrument according to FIGS. 1 and 2.
FIG. 4 shows a schematic side view of the second fastening device according to FIG. 3.
Figure 5:
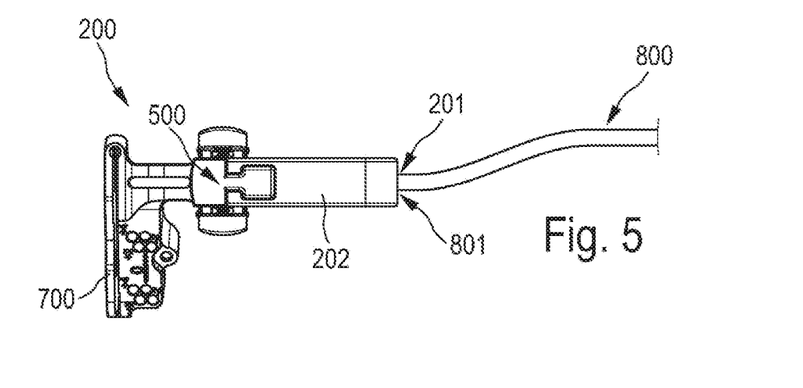
FIG. 5 shows a schematic plan view of the second fastening device according to FIGS. 3 and 4.

The alignment rod 800 is configured for alignment relative to an anterior edge V of the tibia T. In this instance, the alignment rod 800 is connected to the second fastening device 200 in a releasably rigid manner. In FIGS. 1 and 2, the alignment rod 800 is located in an assembled state, in which it is releasably connected to the second fastening device in a rigid manner. In this instance, the releasable connection of the alignment rod 800 to the second fastening device 200 is constructed in a rotationally and pivotably rigid manner. The second fastening device 200 which is shown separately in FIGS. 3 to 5 for greater clarity has a receiving portion 201. The alignment rod 800, which is shown separately in FIGS. 6 to 8, has a fastening portion 801. In the assembled state of the alignment rod 800, the fastening portion 801 is received in a receiving direction A in the receiving portion 201. The alignment rod 800 can be inserted in the receiving portion 201. In this instance, the receiving direction A extends in a proximodistal manner.

Figure 6:
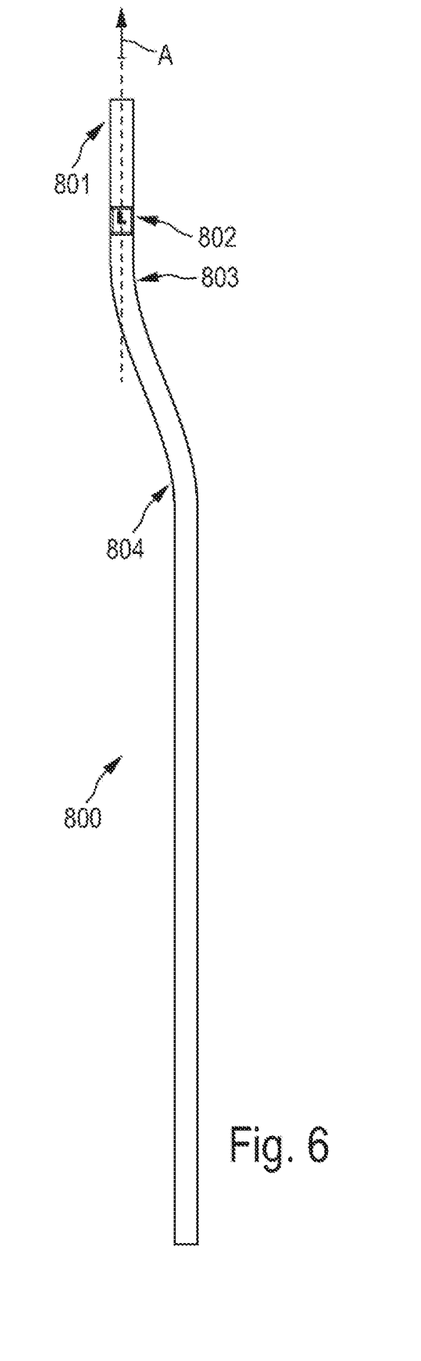
FIG. 6 shows a schematic plan view of a disassembled alignment rod of the surgical instrument according to FIGS. 1 and 2.
Figure 7:
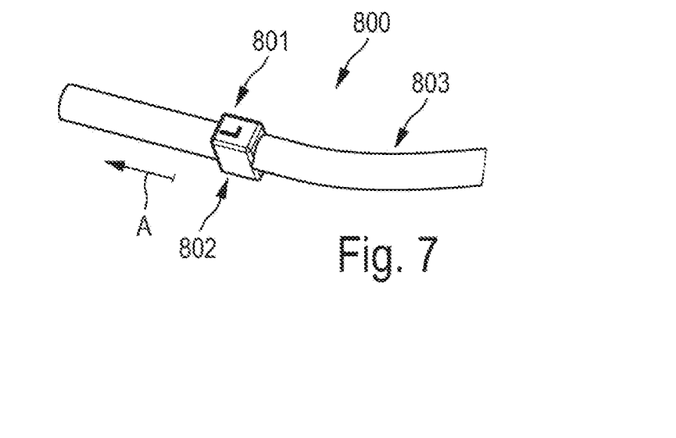
FIG. 7 shows a detail of a schematic perspective view of the alignment rod according to FIG. 6.
Figure 8:
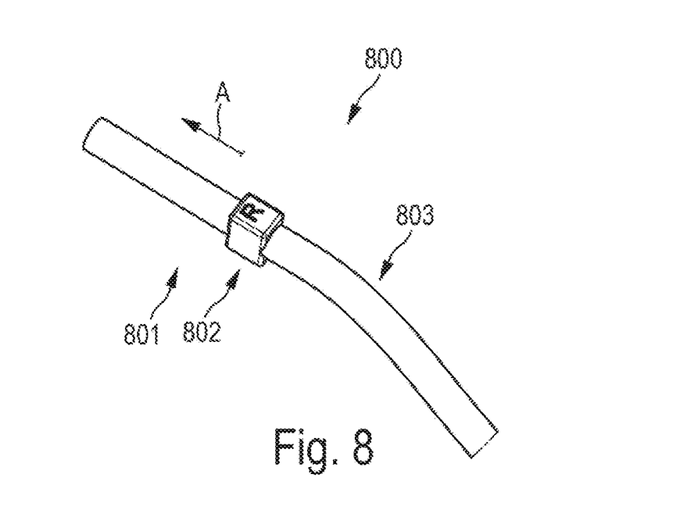
FIG. 8 shows a detail of a schematic, perspective view of the alignment rod according to FIGS. 6 and 7 from another viewing angle.

According to FIGS. 6 to 8, the fastening portion 801 of the alignment rod 800 comprises at least one part-portion 802. The part-portion 802 has a non-round cross section. In this instance, the part-portion 802 has an angular—more specifically a rectangular—cross section. The cross section of the part-portion 802 is orientated perpendicularly to the receiving direction A. The receiving portion 201 of the second fastening device 200 has a shape which is constructed to complement the fastening portion 801 of the alignment rod 800. By means of the non-round cross section and the shape, which is adapted thereto, of the fastening device 200, the releasable rigid connection of the alignment rod 800 to the second fastening device 200 is brought about by positive-locking connection (form-fit). The non-round cross section is constructed in a rotationally symmetrical manner. In this instance, the non-round cross section is constructed in a point-symmetrical manner. As a result of the rotationally symmetrical construction of the cross section, the alignment rod 800 can be received in at least two angular positions relative to the second fastening device 200 in the receiving portion 201. As a result of the point-symmetrical construction of the non-round cross section, the alignment rod 800 can in this instance be mounted in two angular positions which can be rotated relative to each other through 180°.

The alignment rod 800 is in this instance curved in an S-shaped manner. The alignment rod 800 which is curved in an S-shaped manner has a first curved portion 803 and an second curved portion 804. As a result of the two curved portions 803, 804, the alignment rod 800 is in this instance constructed in a S-curved manner. The alignment rod 800 can be used for a knee joint replacement operation both on the right leg and on the left leg, depending on the angular position in which it is mounted on the second fastening device 200. Which of the angular positions is intended for a knee joint replacement operation on the left leg and which is intended for a knee joint replacement operation on the right leg can be identified for the operator with reference to markings shown in FIGS. 7 and 8—L for left and R for right. In order to configure the surgical instrument 1 for an operation on the respective leg, the alignment rod 800 is in this instance releasably connected to the second fastening device 200 in such a manner that the marking which is associated with the respective leg faces in an upward direction. The alignment rod 800 extends in an elongate manner between a proximal end and a distal end. The fastening portion 801 of the alignment rod 800 is arranged at the proximal end.

According to FIGS. 1 to 5, the second fastening device 200 has a handling portion 203. A shaping of the handling portion 203 is adapted to an anatomy of a human hand. This ensures safe and fatigue-free grip of the surgeon, for example, during assembly or disassembly of the alignment rod 800. The second fastening device 200 comprises a base member 202. In this instance, the base member 202 is constructed in a plate-like manner. A recess 204 is arranged in the base member 202. The handling portion 203 is formed by the recess 204. At least one finger of the hand of the user can be received in the recess 204. In this instance, the recess 204 is arranged in a posterior and distal end of the base member 202. Consequently, the recess 204 forms an undercut which during handling of the surgical instrument 1 or the fastening device 200 is positioned as a result of gravitational force in an anteroposterior manner on the hand of the user in order to ensure a secure grip. The base member 202 has in this instance a parallelepipedal shape.

In this instance, the surgical instrument 1 further comprises a display device 900. The display device 900 is configured to display an angular position of the second fastening device 200 in the guiding plane E relative to the first fastening device 100. As a result of the releasable rigid connection of the alignment rod 800 to the second fastening device 200, an angular position of the alignment rod 800 relative to the first fastening device 100 as measured in the guiding plane E corresponds to the angular position indicated by means of the display device 900. The display device 900 comprises at least one reading mark 901. The display device 900 further has at least one scale which cannot, however, be seen in the Figures. The reading mark 901 and the scale show the angular position in a manner familiar to the person skilled in the art in common interaction. The reading mark is in this instance fixedly connected to the first fastening device 100, wherein the scale is fixedly connected to the guiding device 300. Alternatively, however, it is also conceivable for the scale or the reading mark 901 to be connected to the respective component so as to be able to be moved in an adjustable manner relative to the component which carries it in order to configure the display device 900 to be able to be calibrated. A position of the reading mark 901 relative to the scale represents the current angular position of the second fastening device 200 relative to the first fastening device 100 as measured in the guiding plane E. In the assembled state of the alignment rod 800, consequently, the current angular position of the alignment rod 800 relative to the first fastening device 100 can also be read.

The scale has a division with angular increments. The scale may be divided into increments of 1°.

In this instance, the guiding device 300 is in the form of a circular arc guide. The guiding device 300 comprises at least one curved guiding rod 301. In this instance, two such curved guiding rods 301 are provided. The guiding rods 301 are arranged parallel with each other.

The guiding rods 301 are connected to each other at the ends thereof. The guiding device 300 further comprises a guide receiving member 302. In the guide receiving member 302, the guiding rods 301 are received so as to be able to be guided in a slidingly movable manner. In this instance, the guiding receiving member 302 is connected to the first fastening device 100. The guiding rods 301 are connected to the second fastening device 200. Of course, conversely, the at least one guiding rod 301 may also be connected to the first fastening device 100 and the guiding receiving member 302 may also be connected to the second fastening device 200, which is not, however, shown in the Figures. By means of the guiding device 300, the second fastening device 200 is guided in a linearly movable manner along a guiding path C which is elongate in a circular-arc-like manner relative to the first fastening device 100. As a result of the linearly movable guiding along the circular arc path C, the pivoting movability of the first fastening device 100 relative to the second fastening device 200 within the sagittal guiding plane E is achieved.

A first linear guide 400 is further provided. By means of the first linear guide 400, the guiding device 300 is connected to the first fastening device 100. The guiding device 300 is linearly movable in a manner guided by means of the first linear guide 400 relative to the first fastening device 100 in the guiding plane E along a first guiding path L1 which is elongate in an anteroposterior manner. The surgical instrument 1 further comprises a second linear guide 500. The second fastening device 200 is connected to the guiding device 300 by means of the second linear guide 500. The second fastening device 200 and the guiding device 300 are linearly movable in a manner guided relative to each other in the guiding plane E along a second guiding path L2 which is elongate in an anteroposterior manner. The two guiding paths L1 and L2 are located in the same guiding plane E, within which the two fastening devices 100, 200 are guided in a pivotably movable manner relative to each other by means of the guiding device 300. In the intraoperative situation shown in FIGS. 1 and 2, the two guiding paths L1, L2 extend parallel with each other. Both guiding paths L1, L2 extend in this instance in an anteroposterior manner. If the two fastening devices 100, 200 are pivoted relative to each other, the guiding paths L1 and L2 can be positioned in an angular manner with respect to each other. The first linear guide 400 is in the form in the embodiment shown of a cylindrical guide. The second linear guide 500 is in the form of a slotted guide member.

The two fastening devices 100, 200 can be pivoted relative to each other about a pivot axis. The pivot axis is a geometric and/or virtual axis. This pivot axis can be displaced by means of the two linear guides 400, 500. In this instance, the pivot axis always remains orientated perpendicularly to the sagittal guiding plane E. Of course, a corresponding displacement of the pivot axis can also already be achieved with a single linear guide 400, 500. The first linear guide 400 is in this instance arranged at one end of the guiding device 300 and the second linear guide 500 is arranged at the other end of the guiding device 300.

The guiding device 300 which is in the form of a circular arc guide enables a guided relative movement between the second fastening device 200 and the first fastening device 100. The second fastening device 200 is linearly movable in a manner guided relative to the first fastening device 100 along the guiding path C which is elongate in a circular-arc-like manner. In this instance, the second fastening device 200 carries out a rotation and/or pivot movement about a centre of the circular guiding path C. At the centre of the guiding path C which is elongate in a circular-arc-like manner, the pivot axis passes through the sagittal guiding plane E.

The surgical instrument 1 enables a positioning of the tibia cutting block 700 relative to the reference component 600. In this instance, a sagittal inclination of the tibia cutting block 700 can be adjusted without undesirable influencing of a so-called tibia cutting height. The sagittal inclination is also referred to as the slope. In a desirable manner, the positioning of the tibia cutting block 700 is carried out in this case in extension, that is to say, with an extended leg and/or knee joint. In extension, the femur F and the tibia T enclose an angle of 180°. By means of the surgical instrument 1, deviations from the precise extension position in the adjustment of the slope can be taken into account. Consequently, the slope can also be precisely adjusted by means of the surgical instrument 1 when a precise extension position is not present.

A fixing device 303 is further provided. The fixing device 303 is configured for fixing the movability of the guiding device 300. Consequently, by means of the fixing device 303, the angular position between the first and the second fastening device 100, 200 can be fixed. The fixing device 300 brings about a releasable positive-locking (form-fit) and/or non-positive-locking (force-fit) connection between the at least one guiding rod 301 and the guide receiving member 302. For example, the fixing device 303 may bring about a tensioning of the guiding rod 301—in this instance, both guiding rods 301. To this end, the fixing device 303 may have a screwing, clamping, locking or other mechanism. In this instance, the fixing device 302 is configured with a locking mechanism. During a relative movement between the guiding rods 301 and the guiding receiving member 302, the reading mark 901 moves along the scale, in particular along the division of the scale.

In the case of precise extension, the display device 900 acts as a display of the sagittal inclination, that is to say, of the slope, of the tibia cutting block 700.

A use of the surgical instrument 1 for positioning the tibia cutting block 700 will be explained by way of example below.

The positioning is carried out starting from a configuration in which the reference component 600—in the all femur first approach which is followed in this instance, the femoral trial condyle implant 601—is fixed in a manner known to the person skilled in the art to the distal femur F. An orientation or alignment of the femoral trial condyle implant 601 can now be transferred by means of the surgical instrument 1 to the tibia cutting block 700.

To this end, the tibia cutting block 700 is first releasably fastened to the second fastening device 200. The surgical instrument is then referenced at the femur side together with the tibia cutting block 700 which is fastened thereto. To this end, the first fastening device 100 is releasably fastened to the trial condyle implant 601. The releasable fastening of the first fastening device to the femoral trial condyle implant 601 can be produced by means of a plug type connection. In this manner, the configuration which can be seen in FIGS. 1 and 2 can be achieved. If the point at which the pivot axis passes through the sagittal guiding plane E is not located at a desired position referenced to the anatomy of the patient, the position can be re-adjusted by means of the first linear guide 400. If the point is located at its desired position, the alignment rod 800 is aligned with the anterior edge V of the tibia T. The display device 900 then indicates the angular position in which the alignment rod 800 and consequently also the second fastening device 200 together with the tibia cutting block 700 which is secured thereon is located relative to the femoral trial condyle implant 601 and consequently relative to the first fastening device 100. This angular position represents a prevalent flexion angle between the femur F and tibia T or a deviation of this angle from the precise extension. In order to adjust the slope, the second fastening device 200 is now pivoted together with the tibia cutting block 700 which is fastened thereto through precisely the angular value, relative to the sample condyle implant 601 and relative to the first fastening device 100 fastened thereto, which corresponds to the slope. This angular value of the slope can also be read from the display device 900. The tibia cutting height is in this instance not changed since, as described, the positioning of the pivot axis has been carried out beforehand. Of course, the alignment rod 800 in conjunction with the display device 900 can also be used to move the femur F and tibia T into precise extension.

The invention claimed is:

1. A surgical instrument system for use in a knee joint replacement operation, the surgical instrument system comprising:
    a surgical instrument comprising:
    a first fastening device configured for releasable fastening to a reference component which is fitted to a distal femur;
    a second fastening device distally spaced apart from the first fastening device and configured for releasable fastening to a tibia cutting block for guiding cutting on a proximal tibia;
    a guiding device connected at a first end to the first fastening device and at a second end to the second fastening device and by which the second fastening device is pivotably movable in a manner guided relative to the first fastening device in a sagittal guiding plane; and
    an alignment rod configured for alignment with respect to an anterior edge of the tibia, the alignment rod being releasably connected to the second fastening device in a rigid manner;
    a reference component releasably fastened to the first fastening device of the surgical instrument; and
    a tibia cutting block releasably fastened to the second fastening device of the surgical instrument,
    the guiding device having at least one guiding rod that is curved and a guide receiving member in which the at least one guiding rod is received in a state guided in a slidingly movable manner,
    the guide receiving member being connected to the first fastening device,
    the at least one guiding rod being connected to the second fastening device, or vice versa, and
    the second fastening device being guided in a linearly movable manner by the guiding device along a guiding path which is elongate in a circular-arc-like manner relative to the first fastening device.

2. The surgical instrument system according to claim 1, wherein the second fastening device has a receiving portion in which a fastening portion of the alignment rod is received in a receiving direction.

3. The surgical instrument system according to claim 2, wherein the fastening portion of the alignment rod has at least in a part-portion a non-round cross section, wherein the receiving portion of the second fastening device has a shape which is constructed for releasable rigid connection of the alignment rod and the second fastening device so as to complement the fastening portion.

4. The surgical instrument system according to claim 3, wherein the non-round cross section is constructed in a rotationally symmetrical manner so that the alignment rod is receivable for releasable rigid connection to the second fastening device in at least two angular positions relative to the second fastening device in the receiving portion.

5. The surgical instrument system according to claim 1, wherein the alignment rod is bent in an S-shaped manner.

6. The surgical instrument system according to claim 1, wherein the second fastening device has a handling portion, the shape of which is adapted to an anatomy of a hand of a user.

7. The surgical instrument system according to claim 6, wherein the second fastening device comprises a base member on which in order to form the handling portion there is provided a recess which is constructed to receive at least one finger of the hand of the user.

8. The surgical instrument system according to claim 1, further comprising a display device configured to display an angular position of the second fastening device in the sagittal guiding plane relative to the first fastening device.

9. The surgical instrument system according to claim 8, wherein the display device comprises at least one scale and at least one reading mark, wherein the at least one scale is connected to the first fastening device and the at least one reading mark is connected to the guiding device, or vice versa, and wherein a position of the at least one reading mark relative to the at least one scale represents the current angular position of the second fastening device in the sagittal guiding plane relative to the first fastening device.

10. The surgical instrument system according to claim 1, further comprising a first linear guide, by which the guiding device is connected to the first fastening device and is linearly movable in a manner guided relative thereto in the sagittal guiding plane along a first guiding path which is elongate in an anteroposterior manner.

11. The surgical instrument system according to claim 1, further comprising a second linear guide, by which the second fastening device is connected to the guiding device and is linearly movable in a manner guided relative thereto in the sagittal guiding plane along a second guiding path which is elongate in an anteroposterior manner.

12. The surgical instrument system according to claim 1, further comprising a fixing device configured to fix the movability of the guiding device.

* * * * *